United States Patent [19]
Gluckman et al.

[11] Patent Number: 5,922,673
[45] Date of Patent: Jul. 13, 1999

[54] METHOD OF TREATING HYPERTENSION IN PREGNANT MAMMALS

[75] Inventors: Peter David Gluckman; Barbara Madeleine Johnston; Nicole Susan Bassett, all of Auckland, New Zealand

[73] Assignee: Chiron Corporation, Emeryville, Calif.

[21] Appl. No.: 08/809,550

[22] PCT Filed: Sep. 18, 1995

[86] PCT No.: PCT/NZ95/00088

§ 371 Date: May 28, 1997

§ 102(e) Date: May 28, 1997

[87] PCT Pub. No.: WO96/09065

PCT Pub. Date: Mar. 28, 1996

[30] Foreign Application Priority Data

Sep. 21, 1994 [NZ] New Zealand ............. 264498

[51] Int. Cl.⁶ ............. A61K 38/30; C07K 14/65
[52] U.S. Cl. ............................ 514/2; 530/399
[58] Field of Search ................. 514/2; 530/399

[56] References Cited

U.S. PATENT DOCUMENTS

| | | | |
|---|---|---|---|
| 5,179,080 | 1/1993 | Rothkopf | 514/12 |
| 5,378,686 | 1/1995 | Bennett | 514/12 |
| 5,420,111 | 5/1995 | Gluckman et al. | 514/12 |

FOREIGN PATENT DOCUMENTS

| | | | |
|---|---|---|---|
| 2114419 A1 | 12/1993 | Canada | A61K 37/36 |
| WO 87/01038 | 2/1987 | WIPO | A61K 37/24 |
| WO 91/10348 | 7/1991 | WIPO | . |
| WO 91/18621 | 12/1991 | WIPO | A61K 37/24 |
| WO 92/00754 | 1/1992 | WIPO | A61K 37/36 |
| WO 92 02245 | 2/1992 | WIPO | A61K 37/36 |
| WO 93/06839 | 4/1993 | WIPO | A61K 37/00 |

OTHER PUBLICATIONS

Collins, Jr. et al, *Pediatric Research*, vol. 24, No. 6, 1988, pp. 663–667.
Adachi et al, *Chemical Abstracts*, vol. 115, 1991, p. 162.
Diez et al, *Journal of Hypertension* 1994, 12 (suppl 4), pp. S31–S36.
Ross et al, *Biochem. J.* (1989) 258, 267–272.
Ambler et al, *Cardiovascular Research* 1993, 27:1368–1373.
Zapf et al, *J. Clin. Invest.*, vol. 86, Sep. 1990, 952–961.
Guevara–Aguirre et al, *Journal of Clinical Endocrinology and Metabolism*, vol. 82, No. 2, 1997, 629–633.
Hindmarsh et al, *Journal of Clinical Endocrinology and Metabolism*, vol. 82, 1997, 2172–2176.
De Mellow et al, *Biochemical and Biophysical Research Communications*, vol. 156, No. 1, 1988, 199–204.
Medlin on STN. No. 92310684. Conogscenti et al., Minerva Ginecologica, 1991, 43(12), 549–53. Abstract, Dec. 1991.
Medline on STN. No. 92111071. Devoe et al. 'Antepartum Fetal Assessment in Hypertensive Pregnancies', Clinics in Peridnatology, 1991, 18(4), 809–32. Abstract, Dec. 1991.
Medline on STN. No. 83052256. Soma et al. 'Morphlogical Changes in the Hypertensive Placenta' Contributions to Gynecology and Obstetrics, 1982, 9, 58–75. Abstract.
Medline on STN. No. 89306944. Arduini et al. 'Are Blood Flow Velocity Waveforms Related to Umbilical Cord Acid–Base Status in the Human Fetus', Gyneclogic and Obstetric Investigation, 1989, 27(4), 183–7. Abstract.
Medline on STN. No. 88242082. Jungers et al. 'Reflux Nephrophathy and Pregnancy', Ballieres Clinical Obstetrics and Gynaecology, 1987, 1(4), 955–69. Abstract, Dec. 1987.
Adachi et al., Chemical Abstracts, vol. 115, 1991, p. 162.
Ambler et al., J. Cardiovasc. Res. 27: 1368–1373, 1993.

*Primary Examiner*—Cecilia J. Tsang
*Assistant Examiner*—Anish Gupta
*Attorney, Agent, or Firm*—Pollock, Vande Sande & Amernick

[57] ABSTRACT

A method of treating a pregnant mammal (including a human) which comprises administering IGF-1 or an analogue thereof or another hormone (such as growth hormone) which elevates maternal IGF-1 to thereby illicit a reduction of material blood pressure and/or to promote fetal growth and placental function.

21 Claims, No Drawings

METHOD OF TREATING HYPERTENSION IN PREGNANT MAMMALS

TECHNICAL FIELD

The present invention relates to a method of treating high blood pressure or a tendency to be hypertensive in pregnant mammals including humans which aids fetal development.

BACKGROUND ART

Hypertension in pregnancy is, both in man and in other mammals, associated with impaired fetal growth. In man it is frequently associated with a syndrome of proteinuria and edema which is termed "toxaemia of pregnancy" or preeclampsia These pregnancies are complicated by insufficiency and fetal growth retardation. Current therapy is essentially restricted to common anti-hypertensive agents and bed rest which, while reducing the risk of hypertensive crises in the mother, do not correct the fetal growth retardation and reduce the consequent risk of fetal death, stillbirth and the neonatal complications of intrauterine growth retardation. The essence of this invention is that we have found that the administration of IGF-1 in pregnant hypertensive mammals reduces maternal blood pressure and improves placental function and fetal development.

We have previously disclosed that the administration of IGF-1 through part or whole of pregnancy to a maternal mammal overcomes maternal constraint on fetal growth (IGF-1 in Pregnancy: PCT Europe 91912874.4, USA 07/969229, Japan 3-511969, Australia 82052/91, Canada 2087030). We have observed such administration of IGF-1 promoting fetal growth and placental function. However there is nothing in the prior art that would have led us to conclude that there would be a lowering effect on blood pressure. Elsewhere we have disclosed that in non-pregnant animals IGF-1 promotes cardiac output (Ambler et al J Cardiovascular Research 27 1368–1373 1993) and this is associated with maintenance of blood pressure.

In pregnant mammals with hypertension and a predisposition to give birth to growth retarded fetuses with disproportionately large placentas, we have now observed that IGF-1 administration to the mother reverses these changes.

SUMMARY OF INVENTION

In a first aspect the present invention consists in a method of treatment by which IGF-1 is administered to pregnant mammals with hypertension to promote fetal growth and placental function.

In a further aspect the invention consists in a method of treatment by which IGF-1 is administered to pregnant mammals with hypertension to reduce maternal blood pressure.

In still a further aspect the invention consists in a method of treatment by which maternal levels of IGF-1 are elevated either directly by administration of IGF-1 or indirectly by the admission of other hormones which elevate mammal IGF-1 such as growth hormone.

In yet a further aspect the invention consists in a method of treatment where preferably the IGF-1 administered is recombinant human IGF-1 or one of its analogues with alterations to the amino terminal (eg des 1–3 N IGF-1).

In yet a further aspect the invention consists in a method of treatment where the IGF-1 may be administer alone or in combination with binding proteins to alter its half life and bioavailability or in combination with growth hormone.

In still after aspect the present invention consists in a method of treatment where IGF-1 is administered during the latter phase of pregnancy when hypertension is present.

In yet a further aspect the invention consists in a method of treatment where IGF-1 is administered at a dose of 40 to 2000 $\mu$g/kg body weight per day to a pregnant mammal and preferentially in humans at a dose of 40 to 200 $\mu$g/kg/body weight per day.

In yet a further aspect the invention consists in a mode of treatment by which the IGF-1 is administered to a pregnant mammal either continuously by implant or intermittently by subcutaneous or intramuscular, intranasal or oral routes of administration.

In still a further aspect the invention consists in a method of treatment where preferably IGF-1 itself is administered subcutaneously but forms of IGF-1 with increased stability may be given by oral or intranasal route.

In yet a further aspect the invention consists in a mode of treatment where IGF-1 is administered alone or in combination with other antihypertensive treatments.

This invention may also be said broadly to consist in the parts, elements, and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BEST AND VARIOUS MODES FOR CARRYING OUT INVENTION

The invention consists in the foregoing and also envisages constructions of which the following gives examples.

One preferred form of the present invention will now be described with reference to a non limiting example.

Spontaneously hypertensive rats (SHR) are a defined and well studied strain of rat with a propensity to have high blood pressure. They have been extensively used to model human hypertension. They are derived from a Wistar Kyoto (WKY) stain of rat and the appropriate control line is the WKY rat (Wistar Kyoto rat) which is the stain from which the SHR was derived.

SHR or WKY rats were mated under laboratory conditions so that the day of mating was known. At day 10 after mating animals were divided into two groups (n=10 each) to receive either saline or IGF-1. Of these four groups of animals several were determined to be non pregnant leaving reduced numbers in each group. The final numbers in each group were; WKY saline n=7, WKY IGF-1 n=7, SHR saline n=5, SHR IGF-1 n=5. The daily dose of IGF-1 administered was 2 $\mu$g/gm body weight per day. This dose was divided into three equal doses and administered to the mother subcutaneously at 8.00 am, 4.00 pm and 10.00 pm daily. The IGF-1 used was recombinant human IGF-1 provided by Dr Linda Fryklund of Pharmacia AB Stockholm Sweden The saline or IGF-1 treatment was continued until day 20 of pregnancy.

At that age the animals were sacrificed to obtain maternal weights, fetal and placental weights.

On day twenty blood pressure measurements were recorded via a carotid artery cannula on all animals under halothane anaesthetic prior to sacrifice. 10 mins equilibration was allowed to overcome the depressive influence of the anaesthetic.

The following observations were made.

1. Maternal, Placental and Fetal Size

IGF-1 treatment in SHR rats significantly increases circulating IGF-1 concentrations (p=0.031) from 288.92±87.27 ng/ml in saline treated rats to 437.47±102.42 ng/ml in IGF-1 treated rats.

IGF-1 treatment increased mean fetal weight in the SHR rats from 1.79±0.039 g in the saline treated SHR rats to 1.90±0.053 g in the IGF-1 TxSHR rats (p=0.054). A similar trend was observed in fetuses of the saline WKY rats.

IGF-1 treatment in the SHR rats tended to cause a reduction in placental weight compared to that seen in the saline SHR placentae (p=0.096) such that they were of a similar placental weight to that seen in saline treated WKY rats. Placental weight in the saline SHR group was 0.43±0.023 g versus 0.38±0.012 g in the SHR IGF-1 treated group. The saline WKY placenta weight was 0.32 g±0.008 g.

The ratio of fetal to placental weight was significantly increased (p<0.05) from 4.23±0.13 in the saline SHR rats to 5.04±0.14 in IGF-1 treated SHR rats. This was closer to the ratio observed in the saline WKY rats (6.70±0.15) which is presumed to be normal for this strain of rat.

The experimentation was repeated and the Fetal Weight and Placental Weight date can be summarised as follows.

|  | Expt # 1 | Expt # 2 | Combined |
|---|---|---|---|
| FETAL WEIGHT | | | |
| WKY Saline | 2.13 ± 0.021 g (n = 8) | 2.06 ± 0.003 g (n = 5) | 2.11 ± 0.020 g (n = 13) |
| WKY IGF-1 | 2.16 ± 0.039 g (n = 7) | 2.05 ± 0.034 g (n = 5) | 2.11 ± 0.020 g (n = 12) |
| SHR Saline | 1.79 ± 0.039 g (n = 5) | 1.80 ± 0.020 g (n = 5) | 1.80 ± 0.021 g (n = 10) |
| SHR IGF-1 | 1.90 ± 0.024 g (n = 5,p = 0.054) | 1.90 ± 0.067 g (n = 5,p = 0.065) | 1.91 ± 0.034 g (n = 10,p = 0.009) |
| PLACENTAL WEIGHT | | | |
| WKY Saline | 0.32 ± 0.008 g (n = 8) | 0.32 ± 0.009 g (n = 5) | 2.11 ± 0.020 g (n = 13) |
| WKY IGF-1 | 0.32 ± 0.009 g (n = 7) | 0.30 ± 0.005 g (n = 5) | 2.12 ± 0.036 g (n = 12) |
| SHR Saline | 0.43 ± 0.023 g (n = 5) | 0.37 ± 0.004 g (n = 5) | 0.40 ± 0.015 g (n = 10) |
| SHR IGF-1 | 0.38 ± 0.012 g (n = 5,p = 0.096) | 0.36 ± 0.007 g (n = 5,p = 0.085) | 0.37 ± 0.007 g (n = 10,p = 0.065) | p values are group comparisons between saline and IGF-1 treatment in each breed.

2. Blood Pressure

In WKY rats, IGF-1 had no effect on blood pressure or heart rate.

|  | Systolic BP | Diastolic BP | Mean BP | Heart Rate |
|---|---|---|---|---|
| WKY saline | 110 ± 2.0 | 84.1 ± 2.0 | 93.6 ± 1.37 | 360.88 ± 7.16 |
| WKY IGF-1 | 113.6 ± 3.4 | 87.8 ± 5.3 | 96.3 ± 4.6 | 331 ± 12.4 |

In contrast in SHR rats, IGF-1 reduced systolic, diastolic and mean blood pressure but had no effect on heart rate.

|  | Systolic BP | Diastolic BP | Mean BP | Heart Rate |
|---|---|---|---|---|
| SHR saline | 141 ± 6.9 | 109 ± 4 | 119.6 ± 4.9 | 305 ± 17.2 |
| SHR IGF-1 | 128 ± 7.47 | 92.6 ± 10.1 | 104 ± 9.2 | 308.4 ± 12.2 |

This treatment of the SHR rat through the later phase of pregnancy lowered maternal blood pressure, increased fetal growth and increased fetal:placental weight ratio towards that seen in the control WKY strain.

The mode of action of IGF-1 to lower blood pressure is not known. Nor is it known whether it is directly linked to the effects of materially administered IGF-1 on fetal growth and place function. It is well known to those skilled in the art that IGF-1 does not traverse the placental from the maternal to fetal compartment and thus any effect on fetal development is indirect. However the combination of these effects whether interdependent or not is clearly advantageous for fetal development and maternal well being and represents a combination of biological effects which are unique and readily applicable to hypertension of human pregnancy either directly or indirectly.

We claim:

1. A method of treating hypertension in a pregnant mammal or treating a pregnant mammal with tendency to be hypertensive which comprises elevating the IGF-1 maternal levels sufficiently to reduce maternal blood pressure of such mammal by administering to such mammal a member selected from the group consisting of IGF-1, analoque of IGF-1 having biological activity equivalent to IGF-1, growth hormone and mixtures thereof.

2. The method of claim 1 wherein the mammal is a human patient with hypertension and wherein the treating of hypertension results in promoting fetal growth and placental function or reducing maternal blood pressure or both.

3. The method of claim 1 wherein said pregnant mammal has hypertension.

4. A method of claim 1 wherein growth hormone is administered.

5. A method of claim 1 wherein IGF-1 is administered.

6. A method of claim 1 wherein an analogue of IGF-1 having biological activity equivalent to IGF-1 with alterations to the amino terminal is administered.

7. A method of claim 4 wherein des 1–3N IGF-1 is administered.

8. A method of claim 3 where the IGF-1 or analogue thereof having biological activity equivalent to IGF-1 is administered alone, in combination with binding proteins or in combination with growth hormone.

9. A method of claim 1 where IGF-1 is administered during the latter phase of pregnancy when hypertension is present.

10. A method of claim 3, where IGF-1 is administered at a dose of 40 to 2000 $\mu$g/kg body weight per day to a pregnant mammal.

11. A method of claim 3, wherein the mammal is human and IGF-1 is administered at a dose of 40 to 200 $\mu$g/kg bodyweight per day.

12. A method of claim 1 wherein IGF-1 is administered to a pregnant mammal either continuously by implant or intermittently by subcutaneous or intramuscular, intranasal or oral routes of administration.

13. A method of claim 11 where IGF-1 is administered alone or in combination with other antihypertensive treatments.

14. A method of claim 1 wherein IGF-1 itself is administered subcutaneously or a form of IGF-1 with increased stability is administered by the oral or intranasal route.

15. A method of claim 4 where the IGF-1 analogue is administered alone, in combination with binding proteins to alter its half life and bioavailability or in combination with growth hormone.

16. A method of claim 5 where the IGF-1 or analogue thereof is administered alone, in combination with binding proteins to alter its half life and bioavailability or in combination with growth hormone.

17. A method of claim 2 where IGF-1 is administered during the latter phase of pregnancy when hypertension is present.

18. A method of claim 3 where IGF-1 is administered during the latter phase of pregnancy when hypertension is present.

19. A method of claim 4 where IGF-1 is administered during the latter phase of pregnancy when hypertension is present.

20. A method of claim 5 where IGF-1 is administered during the latter phase of pregnancy when hypertension is present.

21. A method of claim 6 where IGF-1 is administered during the latter phase of pregnancy when hypertension is present.

* * * * *